United States Patent
Stahmann et al.

(10) Patent No.: US 7,881,781 B2
(45) Date of Patent: Feb. 1, 2011

(54) THORACIC IMPEDANCE DETECTION WITH BLOOD RESISTIVITY COMPENSATION

(75) Inventors: Jeffrey E. Stahmann, Ramsey, MN (US); John D. Hatlestad, Maplewood, MN (US); Boyce Moon, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 12/628,384

(22) Filed: Dec. 1, 2009

(65) Prior Publication Data
US 2010/0076336 A1 Mar. 25, 2010

Related U.S. Application Data

(63) Continuation of application No. 12/139,948, filed on Jun. 16, 2008, now Pat. No. 7,672,718, which is a continuation of application No. 10/921,503, filed on Aug. 19, 2004, now Pat. No. 7,387,610.

(51) Int. Cl.
*A61B 5/00* (2006.01)
(52) U.S. Cl. ...................... 600/547; 600/481
(58) Field of Classification Search ............... None
See application file for complete search history.

(56) References Cited

U.S. PATENT DOCUMENTS

| | | | |
|---|---|---|---|
| 3,340,867 A | 9/1967 | Kubicek et al. | |
| 3,608,542 A | 9/1971 | Pacela et al. | |
| 3,871,359 A | 3/1975 | Pacela | |
| 4,003,379 A | 1/1977 | Ellinwood, Jr. | |
| 4,059,169 A | 11/1977 | Hagen | |
| 4,146,029 A | 3/1979 | Ellinwood, Jr. | |

(Continued)

FOREIGN PATENT DOCUMENTS

EP 0348271 A1 12/1989

(Continued)

OTHER PUBLICATIONS

"U.S. Appl. No. 10/921,503, Amendment and Response filed Oct. 12, 2007 to Non-Final Office Action mailed Jul. 13, 2007", 21 pgs.

(Continued)

*Primary Examiner*—Robert L Nasser
(74) *Attorney, Agent, or Firm*—Schwegman, Lundberg & Woessner, P.A.

(57) ABSTRACT

This document discusses, among other things, a cardiac rhythm management device or other implantable medical device that uses thoracic impedance to determine how much fluid is present in the thorax, such as for detecting or predicting congestive heart failure, pulmonary edema, pleural effusion, hypotension, or the like. The thoracic fluid amount determined from the thoracic impedance is compensated for changes in blood resistivity, which may result from changes in hematocrit level or other factors. The blood-resistivity-compensated thoracic fluid amount can be stored in the device or transmitted to an external device for storage or display. The blood-resistivity-compensated thoracic fluid amount can also be used to adjust a cardiac pacing, cardiac resynchronization, or other cardiac rhythm management or other therapy to the patient. This document also discusses applications of the devices and methods for predicting or indicating anemia.

30 Claims, 4 Drawing Sheets

U.S. PATENT DOCUMENTS

| | | |
|---|---|---|
| RE30,101 E | 9/1979 | Kubicek et al. |
| 4,271,192 A | 6/1981 | Wurtman et al. |
| 4,308,872 A | 1/1982 | Watson et al. |
| 4,437,469 A | 3/1984 | Djordjevich et al. |
| 4,450,527 A | 5/1984 | Sramek |
| 4,470,987 A | 9/1984 | Wurtman et al. |
| 4,472,420 A | 9/1984 | Toth |
| 4,472,431 A | 9/1984 | Toth |
| 4,559,946 A | 12/1985 | Mower |
| 4,562,843 A | 1/1986 | Djordjevich et al. |
| 4,567,892 A | 2/1986 | Plicchi et al. |
| 4,576,183 A | 3/1986 | Plicchi et al. |
| 4,651,716 A | 3/1987 | Forester et al. |
| 4,686,987 A | 8/1987 | Salo et al. |
| 4,693,253 A | 9/1987 | Adams |
| 4,880,005 A | 11/1989 | Pless et al. |
| 4,884,576 A | 12/1989 | Alt |
| 4,904,472 A | 2/1990 | Belardinelli et al. |
| 4,919,136 A | 4/1990 | Alt |
| 4,980,379 A | 12/1990 | Belardinelli et al. |
| 4,987,897 A | 1/1991 | Funke |
| 5,002,052 A | 3/1991 | Haluska |
| 5,003,976 A | 4/1991 | Alt |
| 5,025,786 A | 6/1991 | Siegel |
| 5,031,629 A | 7/1991 | DeMarzo |
| 5,036,849 A | 8/1991 | Hauck et al. |
| 5,040,536 A | 8/1991 | Riff |
| 5,113,869 A | 5/1992 | Nappholz et al. |
| 5,117,825 A | 6/1992 | Grevious |
| 5,178,154 A | 1/1993 | Ackmann et al. |
| 5,179,947 A | 1/1993 | Meyerson et al. |
| 5,199,428 A | 4/1993 | Obel et al. |
| 5,213,098 A | 5/1993 | Bennett et al. |
| 5,215,083 A | 6/1993 | Drane et al. |
| 5,233,984 A | 8/1993 | Thompson |
| 5,233,985 A | 8/1993 | Hudrlik |
| 5,246,008 A | 9/1993 | Mueller et al. |
| 5,271,395 A | 12/1993 | Wahlstrand et al. |
| 5,273,034 A | 12/1993 | Nilsson |
| 5,282,836 A | 2/1994 | Kreyenhagen et al. |
| 5,282,840 A | 2/1994 | Hudrlik et al. |
| 5,284,136 A | 2/1994 | Hauck et al. |
| 5,292,343 A | 3/1994 | Blanchette et al. |
| 5,300,093 A | 4/1994 | Koestner et al. |
| 5,309,917 A | 5/1994 | Wang et al. |
| 5,313,953 A | 5/1994 | Yomtov et al. |
| 5,324,309 A | 6/1994 | Kallok |
| 5,324,315 A | 6/1994 | Grevious |
| 5,328,471 A | 7/1994 | Slepian |
| 5,342,404 A | 8/1994 | Alt et al. |
| 5,344,429 A | 9/1994 | Smits |
| 5,354,317 A | 10/1994 | Alt |
| 5,354,319 A | 10/1994 | Wyborny et al. |
| 5,355,894 A | 10/1994 | Sivard |
| 5,366,485 A | 11/1994 | Kroll et al. |
| 5,370,665 A | 12/1994 | Hudrlik |
| 5,391,190 A | 2/1995 | Pederson et al. |
| 5,404,877 A | 4/1995 | Nolan et al. |
| 5,405,362 A | 4/1995 | Kramer et al. |
| 5,411,031 A | 5/1995 | Yomtov |
| 5,431,682 A | 7/1995 | Hedberg |
| 5,441,525 A | 8/1995 | Shelton et al. |
| 5,443,073 A | 8/1995 | Wang et al. |
| 5,454,377 A | 10/1995 | Dzwonczyk et al. |
| 5,464,434 A | 11/1995 | Alt |
| 5,479,369 A | 12/1995 | Matsumura et al. |
| 5,484,401 A | 1/1996 | Rodriguez et al. |
| 5,501,701 A | 3/1996 | Markowitz et al. |
| 5,505,209 A | 4/1996 | Reining |
| 5,507,785 A | 4/1996 | Deno |
| 5,522,860 A | 6/1996 | Molin et al. |
| 5,526,808 A | 6/1996 | Kaminsky |
| 5,534,018 A | 7/1996 | Wahlstrand et al. |
| 5,540,728 A | 7/1996 | Shelton et al. |
| 5,562,711 A | 10/1996 | Yerich et al. |
| 5,562,712 A | 10/1996 | Steinhaus et al. |
| 5,593,431 A | 1/1997 | Sheldon |
| 5,607,463 A | 3/1997 | Schwartz et al. |
| 5,626,623 A | 5/1997 | Kieval et al. |
| 5,642,734 A | 7/1997 | Ruben et al. |
| 5,676,686 A | 10/1997 | Jensen et al. |
| 5,685,316 A | 11/1997 | Schookin et al. |
| 5,706,829 A | 1/1998 | Kadri |
| 5,722,999 A | 3/1998 | Snell |
| 5,725,561 A | 3/1998 | Stroebel et al. |
| 5,725,562 A | 3/1998 | Sheldon |
| 5,728,068 A | 3/1998 | Leone et al. |
| 5,732,710 A | 3/1998 | Rabinovich et al. |
| 5,735,284 A | 4/1998 | Tsoglin et al. |
| 5,749,369 A | 5/1998 | Rabinovich et al. |
| 5,749,900 A | 5/1998 | Schroeppel et al. |
| 5,782,774 A | 7/1998 | Shmulewitz |
| 5,782,879 A | 7/1998 | Rosborough et al. |
| 5,782,884 A | 7/1998 | Stotts et al. |
| 5,788,643 A | 8/1998 | Feldman |
| 5,791,349 A | 8/1998 | Shmulewitz |
| 5,800,464 A | 9/1998 | Kieval |
| 5,824,029 A | 10/1998 | Weijand et al. |
| 5,865,760 A | 2/1999 | Lidman et al. |
| 5,874,420 A | 2/1999 | Pelleg |
| 5,876,353 A | 3/1999 | Riff |
| 5,882,352 A | 3/1999 | Duncan et al. |
| 5,913,879 A | 6/1999 | Ferek-Petric et al. |
| 5,919,163 A | 7/1999 | Glickman |
| 5,919,210 A | 7/1999 | Lurie et al. |
| 5,957,861 A | 9/1999 | Combs et al. |
| 5,957,957 A | 9/1999 | Sheldon |
| 5,974,340 A | 10/1999 | Kadhiresan |
| 5,978,705 A | 11/1999 | KenKnight et al. |
| 6,002,963 A | 12/1999 | Mouchawar et al. |
| 6,015,388 A | 1/2000 | Sackner et al. |
| 6,026,324 A | 2/2000 | Carlson |
| 6,035,233 A | 3/2000 | Schroeppel et al. |
| 6,044,297 A | 3/2000 | Sheldon et al. |
| 6,047,203 A | 4/2000 | Sackner et al. |
| 6,049,730 A | 4/2000 | Kristbjarnarson |
| 6,049,735 A | 4/2000 | Hartley et al. |
| 6,075,015 A | 6/2000 | Sestelo et al. |
| 6,076,015 A | 6/2000 | Hartley et al. |
| 6,078,834 A | 6/2000 | Lurie et al. |
| 6,095,987 A | 8/2000 | Shmulewitz et al. |
| 6,104,949 A | 8/2000 | Pitts Crick et al. |
| 6,154,672 A | 11/2000 | Pendekanti et al. |
| 6,161,038 A | 12/2000 | Schookin et al. |
| 6,186,955 B1 | 2/2001 | Baura |
| 6,224,907 B1 | 5/2001 | Davar et al. |
| 6,228,033 B1 | 5/2001 | Koobi et al. |
| 6,266,565 B1 | 7/2001 | Er et al. |
| 6,292,689 B1 | 9/2001 | Wallace et al. |
| 6,298,267 B1 | 10/2001 | Rosborough et al. |
| 6,314,322 B1 | 11/2001 | Rosenberg |
| 6,317,631 B1 | 11/2001 | Ben-Haim et al. |
| 6,336,903 B1 | 1/2002 | Bardy |
| 6,409,675 B1 | 6/2002 | Turcott |
| 6,411,844 B1 | 6/2002 | Kroll et al. |
| 6,438,408 B1 | 8/2002 | Mulligan et al. |
| 6,453,195 B1 | 9/2002 | Thompson |
| 6,459,929 B1 | 10/2002 | Hopper et al. |
| 6,473,640 B1 | 10/2002 | Erlebacher |
| 6,511,438 B2 | 1/2003 | Bernstein et al. |
| 6,512,949 B1 | 1/2003 | Combs et al. |
| 6,527,729 B1 | 3/2003 | Turcott |
| 6,560,481 B1 | 5/2003 | Heethaar et al. |
| 6,561,986 B2 | 5/2003 | Baura et al. |

| | | |
|---|---|---|
| 6,574,506 B2 | 6/2003 | Kramer et al. |
| 6,591,122 B2 | 7/2003 | Schmitt |
| 6,595,927 B2 | 7/2003 | Pitts-Crick et al. |
| 6,600,949 B1 | 7/2003 | Turcott |
| 6,602,201 B1 | 8/2003 | Malecha et al. |
| 6,616,607 B2 | 9/2003 | Hashimoto et al. |
| 6,625,492 B2 | 9/2003 | Florio et al. |
| 6,636,754 B1 | 10/2003 | Baura et al. |
| 6,643,543 B2 | 11/2003 | Takehara et al. |
| 6,665,564 B2 | 12/2003 | Lincoln et al. |
| 6,678,547 B2 | 1/2004 | Carlson et al. |
| 6,714,813 B2 | 3/2004 | Ishigooka et al. |
| 6,719,701 B2 | 4/2004 | Lade |
| 6,738,666 B1 | 5/2004 | Park et al. |
| 6,748,271 B2 | 6/2004 | Spinelli et al. |
| 6,752,765 B1 | 6/2004 | Strobel et al. |
| 6,795,733 B1 | 9/2004 | Lu |
| 6,811,537 B2 | 11/2004 | Bardy |
| 6,829,503 B2 | 12/2004 | Alt |
| 6,829,507 B1 | 12/2004 | Lidman et al. |
| 6,907,288 B2 | 6/2005 | Daum |
| 6,908,437 B2 | 6/2005 | Bardy |
| 6,912,420 B2 | 6/2005 | Scheiner et al. |
| 6,937,900 B1 | 8/2005 | Pianca et al. |
| 6,949,075 B2 | 9/2005 | Hatlesad et al. |
| 7,003,346 B2 | 2/2006 | Singer |
| 7,149,573 B2 | 12/2006 | Wang |
| 7,177,681 B2 | 2/2007 | Zhu et al. |
| 7,191,000 B2 | 3/2007 | Zhu et al. |
| 7,226,422 B2 | 6/2007 | Hatlestad et al. |
| 7,333,854 B1 | 2/2008 | Brewer et al. |
| 7,340,296 B2 | 3/2008 | Stahmann et al. |
| 7,384,395 B2 | 6/2008 | Hatlestsad et al. |
| 7,387,610 B2 | 6/2008 | Stahmann et al. |
| 7,422,560 B2 | 9/2008 | Hatlestsad et al. |
| 7,603,170 B2 | 10/2009 | Hatlestad et al. |
| 7,672,718 B2 | 3/2010 | Stahmann et al. |
| 2001/0020138 A1 | 9/2001 | Ishigooka et al. |
| 2001/0025137 A1 | 9/2001 | Webb et al. |
| 2002/0115939 A1 | 8/2002 | Mulligan et al. |
| 2002/0123674 A1 | 9/2002 | Plicchi et al. |
| 2002/0138014 A1 | 9/2002 | Baura et al. |
| 2002/0147475 A1 | 10/2002 | Scheiner et al. |
| 2002/0147476 A1 | 10/2002 | Daum |
| 2002/0170193 A1 | 11/2002 | Townsend et al. |
| 2002/0193689 A1 | 12/2002 | Bernstein et al. |
| 2003/0023279 A1 | 1/2003 | Spinelli et al. |
| 2003/0028221 A1 | 2/2003 | Zhu et al. |
| 2003/0036773 A1 | 2/2003 | Whitehurst et al. |
| 2003/0055461 A1 | 3/2003 | Girouard et al. |
| 2003/0074029 A1 | 4/2003 | Deno et al. |
| 2003/0105496 A1 | 6/2003 | Yu et al. |
| 2003/0139679 A1 | 7/2003 | Kushnir et al. |
| 2003/0144595 A1 | 7/2003 | Lade |
| 2003/0176896 A1 | 9/2003 | Lincoln et al. |
| 2003/0191503 A1 | 10/2003 | Zhu et al. |
| 2003/0220580 A1 | 11/2003 | Alt |
| 2004/0049235 A1 | 3/2004 | Deno et al. |
| 2004/0073128 A1 | 4/2004 | Hatlestad et al. |
| 2004/0073262 A1 | 4/2004 | Lovett |
| 2004/0086864 A1 | 5/2004 | Lo et al. |
| 2004/0102712 A1 | 5/2004 | Belalcazar et al. |
| 2004/0106962 A1 | 6/2004 | Mai et al. |
| 2004/0116819 A1 | 6/2004 | Alt |
| 2004/0127807 A1 | 7/2004 | Hatlesad et al. |
| 2004/0133079 A1 | 7/2004 | Mazar et al. |
| 2004/0147982 A1 | 7/2004 | Bardy |
| 2004/0172080 A1 | 9/2004 | Stadler et al. |
| 2004/0186523 A1 | 9/2004 | Florio |
| 2004/0215097 A1 | 10/2004 | Wang |
| 2004/0215270 A1 | 10/2004 | Ritscher et al. |
| 2005/0004609 A1 | 1/2005 | Stahmann et al. |
| 2005/0021098 A1 | 1/2005 | Spinelli et al. |
| 2005/0038327 A1 | 2/2005 | Tanaka et al. |
| 2005/0043675 A1 | 2/2005 | Pastore et al. |
| 2005/0080460 A1 | 4/2005 | Wang et al. |
| 2005/0119586 A1 | 6/2005 | Coyle et al. |
| 2005/0123526 A1 | 6/2005 | Shafer |
| 2005/0124908 A1 | 6/2005 | Belalcazar et al. |
| 2005/0137480 A1 | 6/2005 | Alt et al. |
| 2005/0145246 A1 | 7/2005 | Hartley et al. |
| 2005/0171575 A1 | 8/2005 | Dev et al. |
| 2005/0177062 A1 | 8/2005 | Skrabal et al. |
| 2005/0192637 A1 | 9/2005 | Girouard et al. |
| 2005/0283197 A1 | 12/2005 | Daum et al. |
| 2005/0288721 A1 | 12/2005 | Girouard et al. |
| 2006/0020295 A1 | 1/2006 | Brockway et al. |
| 2006/0025699 A1 | 2/2006 | Maile et al. |
| 2006/0041280 A1 | 2/2006 | Stahmann et al. |
| 2006/0134071 A1 | 6/2006 | Ross et al. |
| 2006/0134079 A1 | 6/2006 | Sih et al. |
| 2006/0135886 A1 | 6/2006 | Lippert et al. |
| 2006/0224201 A1 | 10/2006 | Hettrick et al. |
| 2006/0241512 A1 | 10/2006 | Kwok et al. |
| 2006/0241513 A1 | 10/2006 | Hatlestad et al. |
| 2006/0258952 A1 | 11/2006 | Stahmann et al. |
| 2006/0264776 A1 | 11/2006 | Stahmann et al. |
| 2006/0282120 A1 | 12/2006 | Sih |
| 2006/0293609 A1 | 12/2006 | Stahmann et al. |
| 2007/0027487 A1 | 2/2007 | Mika et al. |
| 2007/0054871 A1 | 3/2007 | Pastore et al. |
| 2007/0106130 A1 | 5/2007 | Hatlestsad et al. |
| 2007/0118054 A1 | 5/2007 | Pinhas et al. |
| 2007/0129643 A1 | 6/2007 | Kwok et al. |
| 2008/0045852 A1 | 2/2008 | Hatlestad et al. |
| 2008/0108907 A1 | 5/2008 | Stahmann et al. |
| 2008/0249433 A1 | 10/2008 | Stahmann et al. |
| 2009/0005697 A1 | 1/2009 | Hatlestsad et al. |
| 2009/0326599 A1 | 12/2009 | Hatlestad et al. |

FOREIGN PATENT DOCUMENTS

| | | |
|---|---|---|
| EP | 0584388 A1 | 3/1994 |
| EP | 0620420 A1 | 10/1994 |
| EP | 0663219 A1 | 7/1995 |
| EP | 0985374 A2 | 3/2000 |
| EP | 0985429 A2 | 3/2000 |
| EP | 1057498 A2 | 12/2000 |
| EP | 1078597 A2 | 2/2001 |
| EP | 1151719 A2 | 11/2001 |
| EP | 0606301 B1 | 12/2001 |
| EP | 1238630 A2 | 9/2002 |
| EP | 1247487 A1 | 10/2002 |
| EP | 1275342 A2 | 1/2003 |
| EP | 771172 B1 | 4/2003 |
| EP | 1115350 B1 | 8/2003 |
| EP | 1011803 B1 | 9/2004 |
| EP | 0985374 B1 | 12/2004 |
| EP | 0985429 B1 | 12/2004 |
| WO | WO-8400227 A1 | 1/1984 |
| WO | WO-9304627 A1 | 3/1993 |
| WO | WO-9601586 A1 | 1/1996 |
| WO | WO-9737591 A1 | 10/1997 |
| WO | WO-9738628 A1 | 10/1997 |
| WO | WO-9800197 A1 | 1/1998 |
| WO | WO-9833554 A1 | 8/1998 |
| WO | WO-9851211 A1 | 11/1998 |
| WO | WO-0018317 A2 | 4/2000 |
| WO | WO-0119426 A2 | 3/2001 |
| WO | WO-0141638 A1 | 6/2001 |
| WO | WO-02053026 A2 | 7/2002 |
| WO | WO-02053228 A1 | 7/2002 |
| WO | WO-03020364 A2 | 3/2003 |
| WO | WO 2004012815 | 2/2004 |
| WO | WO-2004047638 A1 | 6/2004 |
| WO | WO-2004050178 A1 | 6/2004 |

| WO | WO-2004060166 A2 | 7/2004 |
| WO | WO-2004095306 A1 | 11/2004 |
| WO | WO-2005046472 A2 | 5/2005 |

OTHER PUBLICATIONS

"U.S. Appl. No. 10/921,503, Notice of Allowance mailed Jan. 31, 2008", 8 pgs.

"U.S. Appl. No. 10/921,503, Response to Restriction Requirement and Preliminary Amendment filed Apr. 9, 2007", 19 pgs.

"U.S. Appl. No. 10/921,503, Restriction Requirement mailed Mar. 7, 2007", 6 pgs.

"U.S. Appl. No. 10/921,503, Supplemental Amendment and Response filed Oct. 25, 2007 to Office Action mailed Jul. 13, 2007", 24 pgs.

"U.S. Appl. No. 10/921,503, Non-Final Office Action mailed Jul. 13, 2007", 5 pgs.

"U.S. Appl. No. 11/126,689, Advisory Action mailed Aug. 27, 2007", 3 pgs.

"U.S. Appl. No. 11/126,689, Final Office Action mailed Jun. 14, 2007", 13 pgs.

"U.S. Appl. No. 11/126,689, Non-Final Office Action mailed Jan. 3, 2007", 9 pgs.

"U.S. Appl. No. 11/126,689, Non-Final Office Action mailed Feb. 6, 2009", 14 pgs.

"U.S. Appl. No. 11/126,689, Non-Final Office Action mailed Jul. 21, 2008", 6 pgs.

"U.S. Appl. No. 11/126,689, Non-Final Office Action mailed Oct. 19, 2007", 11 pgs.

"U.S. Appl. No. 11/126,689, Response and Preliminary Amendment filed Oct. 10, 2006 to Restriction Requirement mailed Sep. 8, 2006", 12 pgs.

"U.S. Appl. No. 11/126,689, Response filed Jan. 22, 2008 to Non-Final Office Action mailed Oct. 19, 2007", 23 pgs.

"U.S. Appl. No. 11/126,689, Response filed Apr. 3, 2007 to Non-Final Office Action mailed Jan. 3, 2007", 22 pgs.

"U.S. Appl. No. 11/126,689, Response filed Aug. 14, 2007 to Final Office Action mailed Jun. 14, 2007", 13 pgs.

"U.S. Appl. No. 11/126,689, Response filed Oct. 21, 2008 to Non Final Office Action mailed Jul. 21, 2008", 13 pgs.

"U.S. Appl. No. 11/126,689, Restriction Requirement mailed Sep. 8, 2006", 5 pgs.

"U.S. Appl. No. 11/132,109, Decision from Pre-Appeal Brief Review mailed Aug. 9, 2007", 2 pgs.

"U.S. Appl. No. 11/132,109, Final Office Action mailed Jan. 22, 2007", 13 pgs.

"U.S. Appl. No. 11/132,109, Non-Final Office Action Mailed Jul. 7, 2006", 10 pgs.

"U.S. Appl. No. 11/132,109, Notice of Allowance mailed Oct. 5, 2007", 10 pgs.

"U.S. Appl. No. 11/132,109, Pre-Appeal Brief Request for Review filed Apr. 23, 2007", 5 pgs.

"U.S. Appl. No. 11/132,109, Response filed Oct. 10, 2006 to Non-Final Office Action mailed Jul. 7, 2006", 20 pgs.

"U.S. Appl. No. 12/139,948 Non-Final Office Action mailed Feb. 6, 2009", 6 pgs.

"U.S. Appl. No. 12/139,948, Notice of Allowance mailed Sep. 4, 2009", 6 pgs.

"U.S. Appl. No. 12/139,948, Response filed Apr. 27, 2009 to Non Final Office Action mailed Feb. 6, 2009", 8 pgs.

"Heart Sounds", [online]. Retrieved from the Internet: <URL: http://www.chfpatients.com/faq/s3s4.htm>, 4 pgs.

"Medtronic Announces European Release Of Innovative InSync Sentry Cardiac Resynchronization Therapy Defibrillator", http://www.medtronic.com/newsroom/news_20040614a.html, (2004).

"Medtronic: InSync tm Sentry 7298: Dual Chamber Implantable Cardioverter Defibrillator with Cardiac Resynchronization Therapy (VVE-DDR) and Opti-Vol tm Fluid Monitoring: Reference Manual", (2004), 420 pgs.

Adamicza, A., et al., "Changes in transthoracic electrical impedance during endotoxemia in dogs", Acta Physiol Hung., 85(4), (1997-98), 291-302.

Adamicza, A., et al., "Investigation of the thoracic electrical impedance during endotoxemia in dogs", Acta Chir Hung., 36(1-4), (1997), 1-3.

Alt, Eckhard, et al., "Control of Pacemaker Rate by Impedance-based Respiratory Minute Ventilation", Chest, 92(2), (Aug. 1987), 247-252.

Baarends, E. M., et al., "Body-water compartments measured by bio-electrical impedance spectroscopy in patients with chronic obstructive pulmonary disease", Clinical. Nutrition, 17(1), (Feb. 1998), 15-22.

Belalcazar, Andres, et al., "Improved lung edema monitoring with coronary vein pacing leads", Pacing and Clinical Electrophysiology, 26(4 pt. II), Abstract 18, (Apr. 2003), 933.

Belalcazar, Andres, et al., "Improved lung edema monitoring with coronary vein pacing leads: a simulation study", Physiological Measurement, vol. 25, (2004), 475-487.

Berman, Irwin R, et al., "Transthoracic electrical impedance s a guide to intravascular overload", Archives of Surgery, 102(1), (Jan. 1971), 61-64.

Bradbury, M. G., et al., "Assessment of the sensitivity of bioimpedance to volume changes in body water", Pediatr Nephrol., 9(3), (Jun. 1995), 337-40.

Bussmann, W. D., et al., "Effect of Nitroglycerin Sublingualiy in the Emergency Management of "Classical" Pulmonary Oedema.", Deutsche medizinische Wochenschrift, 102(10), (1946), 9 pgs.

Campbell, J. H, et al., "Clinical applications of electrical impedance tomography in the monitoring of changes in intrathoracic fluid volumes", Physiol. Meas., vol. 15, (1994), A217-A222.

Campbell, J. H, et al., "Detection of changes in intrathoracic fluid in man using electrical impedance tomography", Clinical Science, vol. 87, (1994), 97-101.

Charach, Gideon, et al., "Transthoracic monitoring of the impedance of the right lung in patients with cardiogenic pulmonary edema", Critical Care Medicine, 29(6), (Jun. 2001), 1137-44.

Chiolero, R. L., et al., "Assessment of changes in body water by bioimpedance in acutely ill surgical patients.", Intensive Care Medicine, 18(6), (1992), 322-6.

Defaye, P., et al., "Automatic Recognition of Abnormal Respiratory Events During Sleep by a Pacemaker Transthoracic Impedance Sensor", Journal of Cardiovascular Electrophysiology, 15(9), (Sep. 2004), 1034-40.

Denniston, J. C, et al., "Factors Influencing the measurement of stroke volume by electrical impedance", Physiology (1372-1377), Abstract No. 1373, 463.

Denniston, J. C., et al., "Measurement of pleural effusion by electrical impedance.", Journal of Applied Physiology, 38(5), (May 1975), 851-7.

Ebert, T J, et al., "The use of thoracic impedance for determining thoracic blood volume changes in man", Aviat Space Environ Med., 57(1), (Jan. 1986), 49-53.

Ellenbogen, Kenneth A, et al., "Rate-adaptive pacing based on impedance-derived minute ventilation", Clinical Cardiac Pacing, Philadelphia : Saunders, (1995), 219-233.

Ellenbogen, Kenneth A, et al., "The Electrode-Tissue Interface and the Foreign Body Response", Clinical Cardiac Pacing, Philadelphia : Saunders, (1995), 22-23.

Fein, Alan, et al., "Evaluation of Transthoracic Electrical Impedance in the Diagnosis of Pulmonary Edema", Circulation, 60(5), (Nov. 1979), 1156-1160.

Fleischhauer, J., et al., "Electrical resistances of interstitial and microvascular space as determinants of the extracellular electrical field and velocity of propagation in ventricular myocardium", Circulation, 92(3), (Aug. 1, 1995), 587-594.

Foreman, B, et al., "Intra-thoracic impedance: a surrogate measure of thoracic fluid—fluid accumulation status trial (FAST)", Journal of Cardiac Failure, 10(4 Suppl), Abstract 251, (2004), S86.

Forro, M., et al., "Total body water and ECFV measured using bioelectrical impedance analysis and indicator dilution in horses", Journal of Applied Physiology, 89(2), (Aug. 2000), 663-71.

Frerichs, I., et al., "Electrical impedance tomography in monitoring experimental lung injury", Intensive Care Med., 24(8), (Aug. 1998), 829-36.

Garland, J. S., et al., "Measurement of extravascular lung water in hemodialysis patients using blood ultrasound velocity and optical density dilution.", *ASAIO Journal 2002* 48(4), (Jul.-Aug. 2002), 398-403.

Goovaerts, H. G, et al., "Microprocessor-based system for measurement of electrical impedances during haemodialysis and in postoperative care", *Medical & Biological Engineering & Computing*, vol. 26, (Jan. 1988), 75-80.

Gotshall, R W, et al., "Bioelectric impedance as an index of thoracic fluid.", *Aviation Space and Environmental Medicine*, 70(1), (Jan. 1999), 58-61.

Grimbert, F., et al., "Pulmonary water and thoracic impedance. Evaluation of a measurement technic", *Annales de L'anesthésiologie Française*, 16 Spec No. 2-3, French, (1975), 157-63.

Harris, N. D., et al., "Applications of applied potential tomography (APT) in respiratory medicine", *Clinical Physics and Physiological Measurement*, 8 Suppl A, (1987), 155-65.

Hatlestad, J. D, et al., "Physiological Response to Posture Change", U.S. Appl. No. 11/466,925, filed Aug. 24, 2006, 21 pgs.

Hatlestad, John D, et al., "Calibration of Impedance Monitoring of Respiratory Volumes Using Thoracic D.C. Impedance", U.S. Appl. No. 11/114,661, filed Apr. 26, 2005, 31 pgs.

Hoon, Raghunath Singh, et al., "Changes in Transthoracic electrical impedance at high altitude", *British Heart Journal*, vol. 39, (1977), 61-66.

Hull, E. T, et al., "The Transthoracic Impedance Method for the Determination of the Degree and Change in Extravascular Water", *Acta Tuberc. Pneumol. Belg.*, 68(4), (1977), 369-377.

Hull, E. T, et al., "Transthoracic electrical impedance: artifacts associated with electrode movement", *Resuscitation*, 6(2), (1978), 115-124.

Ishibe, Y., et al., "Transthoracic electrical impedance method for measurement of pulmonary edema in vivo", *Masui*; 27(13), Japanese, (Dec. 1978), 1559-67.

Joekes, A. M, et al., "Impedance Cardiography—Its value in an intensive care unit", *D) Materiels et techniques/Cardiocirculatory Equipment and Technics*, Abstract No. 141, 1 Page.

Keller, Guido, et al., "Monitoring of Pulmonary Fluid Volume and Stroke Volume by Impedance Cardiography in Patients on Hemodialysis", *Chest*, 72(1), (Jul. 1977), 56-62.

Khan, Mahfooz R, et al., "Quantitative electrical-impedance plethysmography for pulmonary oedema", *Medical & Biological Engineering & Computing*, vol. 15, (Nov. 1977), 627-633.

Kiesler, T. W., et al., "Impedance cardiography by use of a spot-electrode array to track changes in cardiac output in anesthetized dogs.", *Journal of the American Veterinary Medical Association*, 196(11), (Jun. 1, 1990), 1804-10.

Koizumi, T., "Changes of transthoracic impedance (zinf 0 and deltaz) in newborn infants", *Acta Neonatol. Jpn.*, 14(3), (1978), 335-340.

Kunst, P. W., et al., "Electrical impedance tomography in the assessment of extravascular lung water in noncardiogenic acute respiratory failure", *Chest*, 116(6), (Dec. 1999), 1695-702.

Kurimoto, et al., "A Case of Pulmonary Edema in a Horse Treated for Cardiac Ailments", *J. Equine Sci*, vol. 13 No. 1., (2002), 29-34.

Kusumoto, Fred M, et al., "Medical Progress: Cardiac Pacing", *New England Journal of Medicine*, 334(2), (Jan. 11, 1996), 89-98.

Larsen, F., et al., "Influence of furosemide and body posture on transthoracic electrical impedance in AMI", *Chest*, 90(5), (733-7), Nov. 1986.

Laszlo, Z., et al., "Cardiovascular and Hormonal Changes with Different Angles of Head-up Tilt in Men", *Physiol. Res.*, vol. 50, (2001), 71-82.

Lau, C P, et al., "Rate-responsive pacing with a pacemaker that detects respiratory rate (Biorate): clinical advantages and complications", *Clinical Cardiology*, 11(5), (May 1988), 318-24.

Lau, C. P., "The range of sensors and algorithms used in rate adaptive cardiac pacing", *Pacing and clinical electrophysiology: PACE*, 15(8), (Aug. 1992), 1177-211.

Leung, Zoe Kc, et al., "Feasibility of an automatic atrial and ventricular threshold determination using transthoracic using impedance", *Pacing and Clinical Electrophysiology*, vol. 19, Part II, Abstract 263, (Apr. 1996), 631.

Luepker, R. V., et al., "Transthoracic Electrical Impedance: Quantitative Evaluation of a Non-Invasive Measure of Thoracic Fluid Volume", *American Heart Journal*, 85(1), (Jan. 1973), 83-93.

Mai, J., et al., "Enhanced Rate Response Algorithm for Orthostatic Compensation Pacing", *Pacing Clin Electrophysiol*, 23, Naspe Abstracts, Abstract No. 678, (Apr. 2000), 722.

McCarty, Richard N, et al., "Assessment of pulmonary edema in acute congestive heart failure with impedance cardiography", *J Am Osteopath Assoc.*, 74(9), (May 1975), 879.

McNamee, James E, et al., "Peribronchial electrical admittance measures lung edema and congestion in the dog", *Special Communications, Electrical Admittance and Pulmonary Edema*, 337-341.

Newell, J. C., et al., "Assessment of acute pulmonary edema in dogs by electrical impedance imaging", *IEEE Transactions on Biomedical Engineering*, 43(2), (Feb. 1996), 133-138.

Nierman, D. M., et al., "Evaluation of transthoracic bioelectrical impedance analysis in monitoring lung water during diuresis", *Applied Cardiopulmonary Pathophysiology*, 7(1), (1997), 57-62.

Nierman, David M, "Transthoracic Bioimpedance Can Measure Extravascular Lung Water in Acute Lung Injury1", *Journal of Surgical Research 65*, Article No. 0350, (1996), 101-108.

Noble, T. J., et al., "Diuretic induced change in lung water assessed by electrical impedance tomography", *Physiol Meas.*, 21(1), (Feb. 2000), 155-63.

Nukiwa, Toshihiro, et al., "Responses of Serum and Lung Angiotensin-Converting Enzyme Activities in the Early Phase of Pulmonary Damage Induced by Oleic Acid in Dogs", *Am Rev Respir Dis.*, 126(6), (Dec. 1982), 1080-1086.

Petersen, J. R., et al., "Electrical impedance measured changes in thoracic fluid content during thoracentesis", *Clin Physiol.*, 14(4), (Jul. 1994), 459-66.

Petersen, M E, et al., "Cardiac pacing for vasovagal syncope: a reasonable therapeutic option?", *Pacing Clin Electrophysiol.*, 20(3 Pt 2), (Mar. 1997), 824-6.

Platia, Edward V, et al., "Time Course of Transvenous Pacemaker Stimulation Impedance, Capture Threshold, and Electrogram Amplitude", *Pacing Clin Electrophysiol.*, 9(5), (Sep./Oct. 19), 620-625.

Pomerantz, M, et al., "Transthoracic electrical impedance for the early detection of pulmonary edema", *Surgery*, 66(1), (Jul. 1969), 260-8.

Raaijmakers, E., et al., "Estimation of non-cardiogenic pulmonary oedema using dual-frequency electrical impedance.", *Medical & Biological Engineering & Computing*, 36(4), (Jul. 1998), 461-6.

Raggueneau, J. L, et al., "Monitoring of intracellular and extracellular hydric compartments by body impedance", *Anesth Anal. Rean*, vol. 36, (1979), 439-443.

Ramos, Marcos U, et al., "Transthoracic electric impedance. A clinical guide of pulmonary fluid accumulation in congestive heart failure", *Minnesota Medicine*, 58(9), (Sep, 1975), 671-676.

Rosborough, John P, et al., "Electrical Therapy for Pulseless Electrical Activity", *NASPE*, 23(4), Part II, Abstract, (Apr. 2000), 591.

Saunders, Charles E, "The Use of Transthoracic Electrical Bioimpedance in Assessing Thoracic Fluid Status in Emergency Department Patients", *American Journal of Emergency Medicine*, 6(4), (Jul. 1988), 337-340.

Schuster, C. J, et al., "Application of Impedance Cardiography in Critical Care Medicine", *Resuscitation*, vol. 11, (1984), 255-274.

Schwartzman, David, et al., "Serial Defibrillation Lead Impedance in Patients with Epicardial and Nonthoracotomy Lead Systems", *Journal of Cardiovascular Electrophysiology*, 7(8), (Aug. 1996), 697-703.

Segev, G., et al., "B-Type Natriuretic Peptide: A Novel Clinical Tool for Diagnosis and Management of Heart Failure", *Hospital Physician*, ., (Sep. 2003), 19-24.

Shochat, M., et al., "Internal thoracic impedance monitoring: a new prospect in acute heart failure", *European Heart Journal*, 25(Supp), (Aug.-Sep. 2004), p. 72-72.

Shoemaker, William C, et al., "Multicenter trial of a new thoracic electrical bioimpedance device for cardiac output estimation", *Critical Care Medicine*, 22(12), (Dec. 1994), 1907-1912.

Smith, R. M., et al., "Canine thoracic electrical impedance with changes in pulmonary gas and blood volumes.", *Journal of Applied Physiology*, 53(6), (Dec. 1982), 1608-13.

Spinale, F. G., et al., "Noninvasive estimation of extravascular lung water using bioimpedance.", *The Journal of Surgical Research*, 47(6), (Dec. 1989), 535-40.

Spinelli, J. C., "Method and System for Treatment of Neurocardiogenic Syncope", U.S. Appl. No. 10/862,831, filed Jun. 7, 2004, 15 pgs.

Sra, J S, et al., "Cardiac pacing during neurocardiogenic (vasovagal) syncope", *J Cardiovasc Electrophysiol.*, 6(9), (Sep. 1995), 751-60.

Stadler, R., et al., "Automated detection of decreases in intrathoracic impedance to predict CHF hospitalization", Abstract 263, 26(4 pt II), Abstract 16, (Apr. 2003), 932.

Stahmann, Jeffrey E, et al., "Detection of Pleural Effusion Using Transthoracic Impedance", U.S. Appl. No. 11/132,109, filed May 18, 2005, 47 pgs.

Staub, N. C., "The measurement of lung water content.", *The Journal of Microwave Power*, 18(3), (Sep. 1983), 259-63.

Tang, W., "Assessment of total body water using bioelectrical impedance analysis in neonates receiving intensive care",*Arch Dis Child Fetal Neonatal Ed.*, 77(2), (Sep. 1997), F123-6.

Tempel, G., et al., "Transthoracic electrical impendance in anaesthesia and intensive care.", *Resuscitation*, 6(2), (1978), 97-105.

Thakur, Ranjan K, et al., "Pericardial Effusion Increases Defibrillation Energy Requirement", *Pacing Clin Electrophysiol.*, 16(6), (Jun. 1993), 1227-1230.

Vainshtein, G. B, et al., "The Functioning of the Cerebral Circulation System in Hyperthermia in Rabbits", *Fiziol Zh SSSR Im I M Sechenova*, 75(11), (Nov. 1989), 1608-1614.

Van De Water, Joseph M, et al., "Monitoring the Chest with Impedance", *Chest*, 64(5), (Nov. 1973), 597-603.

Viirola, H, "Controlled growth of antimony-doped tin dioxide thin films by atomic layer epitaxy", *Thin Solid Films*, 251, (Nov. 1994), 127-135.

Viirola, H, et al., "Controlled growth of tin dioxide thin films by atomic layer epitaxy", *Thin Solid Films*, 249(2), (Sep. 1994), 144-149.

Visokay, M R, "Application of HfSiON as a gate dielectric material", *Applied Physics Letters*, 80(17), (Apr. 2002), 3183-3185.

Wang, L., et al., "Impedance based prediction of CHF admission precedes symptoms in heart failure patients", *Heartrhythm : the official journal of the Heart Rhythm Society*, 1(Suppl 1), Abstract 679, (2004), S213.

Wang, L., et al., "Prediction of CHF hospitalization by ambulatory intrathoracic impedance measurement in CHF patients is feasible using pacemaker or ICD lead systems", *Pacing and Clinical Electrophysiology*, 26(4 pt. II), Abstract 123, (Apr. 2003), 959.

Wang, Li, et al., "Multiple Sources of the Impedance Cardiogram Based on 3-D Finite Difference Human Thorax Models", *IEEE Transactions on Biomedical Engineering*, 42(2), (Feb. 1995), 141-148.

Wuerz, Richard C, et al., "Effects of prehospital medications on mortality and length of stay in congestive heart failure", *Annals of Emergency Medicine*, 21(6), (Jun. 1992), 669-74.

Yu, C., et al., "Changes in device based thoracic impedance in decompensating congestive heart failure", *Circulation*, 104(17 supplement)., Abstract 1994, (2001), II-419.

Yu, C. M., et al., "Correlation of device-based intra-thoracic impedance and patient fluid status during intravenous diuretic therapy in acute CHF", *Euopean Heart Journal*, 23(Abstract Supplement), (2002), 158.

Yu, C., et al., "Device-based intra-thoracic impedance correlates with fluid status and provides automaticed prediction of CHF hospitalization", *Journal of Cardiac Failure*, 10(4 Suppl), Abstract 354, (2004), S113.

Yu, C., et al., "Early warning of CHF hospitalization by intra-thoracic impedance measurement in CHF patients with pacemakers", *Pacing and Clinical Electrophysiology: PACE*, 24(4 pt II), Abstract 19, (2002), 527.

Yu, C. M., et al., "Impedance measurements from implanted devices provide automated prediction of CHF hospitalization", *European Heart Journal*, 25(Supp), (Aug.-Sep. 2004), p. 27-27.

Yu, C. M., et al., "Intrathoracic impedance: A surrogate measure of fluid retention and predictor of hospitalization in patients with heart failure", *Journal of the American College of Cardiology*, 41(6 Supplement A), Abstract 1206-70, (2003), 210A.

Zellner, J. L., et al., "Bioimpedance: a novel method for the determination of extravascular lung water.", *The Journal of Surgical Research*, 48(5), (May 1990), 454-9.

Zima, E., "Intracardiac impedance in biventricular electrode configuration for left ventricular volume monitoring", *European Heart Journal*, 25(Supp), (Aug.-Sep. 2004), p. 165-165.

"U.S. Appl. No. 11/126,689, Final Office Action mailed Mar. 12, 2010", 16 pgs.

"U.S. Appl. No. 11/126,689, Response filed Oct. 19, 2009 to Restriction Requirement mailed Sep. 17, 2009", 16 pgs.

"U.S. Appl. No. 11/972,405, Non-Final Office Action mailed Apr. 12, 2010", 10 pgs.

"U.S. Appl. No. 12/204,152, Non-Final Office Action mailed Mar. 19, 2010", 5 pgs.

"U.S. Appl. No. 12/204,152, Notice of Allowance mailed Jun. 23, 2010", 4 pgs.

"U.S. Appl. No. 12/204,152, Response filed May 24, 2010 to Non Final Office Action mailed Mar. 19, 2010", 7 pgs.

THORACIC IMPEDANCE DETECTION WITH BLOOD RESISTIVITY COMPENSATION

CROSS REFERENCE TO RELATED APPLICATION

This application is a continuation of U.S. application Ser. No. 12/139,948, now U.S. Pat. 7,672,718, filed Jun. 16, 2008, which is a continuation of U.S. application No. 10/921,503, filed Aug. 19, 2004, now U.S. Pat. No. 7,387,610, the specifications of which are herein incorporated by reference.

TECHNICAL FIELD

This document pertains generally to implantable medical devices and more particularly, but not by way of limitation, to congestive heart failure (CHF) thoracic fluid detection and other thoracic impedance systems, devices, or methods that compensate or correct for changes in blood resistivity.

BACKGROUND

Variations in how much fluid is present in a person's thorax can take various forms and can have different causes. Eating salty foods can result in retaining excessive fluid in the thorax and elsewhere. Posture changes can also affect the amount of thoracic fluid. For example, moving from supine to standing can shift intravascular fluid away from the thorax toward the lower extremities.

Another example is pulmonary edema, which results in buildup of extravascular fluid in the lungs. In pulmonary edema, fluid accumulates in extracellular spaces, such as the spaces between lung tissue cells. One cause of pulmonary edema is congestive heart failure (CHF), which is also sometimes referred to as "chronic heart failure," or as "heart failure." CHF can be conceptualized as an enlarged weakened portion of heart muscle. The impaired heart muscle results in poor cardiac output of blood. As a result of such poor blood circulation, blood tends to pool in blood vessels in the lungs. This intravascular fluid buildup, in turn, results in the extravascular fluid buildup mentioned above. In sum, pulmonary edema can be one important condition associated with CHF.

Yet another example of thoracic fluid accumulation is pleural effusion, which is the buildup of extravascular fluid in the space between the lungs and the rib cage. Pleural effusion can also result from CHF because, as discussed above, intravascular fluid buildup can result in the extravascular interstitial fluid buildup. The extravascular fluid buildup of pulmonary edema can, in turn, result in the extravascular fluid buildup of pleural effusion.

CHF may also activate several physiological compensatory mechanisms. Such compensatory mechanisms are aimed at correcting the reduced cardiac output. For example, the heart muscle may stretch to increase its contractile power. Heart muscle mass may also increase. This is referred to as "hypertrophy." The ventricle may also change its shape as another compensatory response. In another example, a neuro-endocrine response may provide an adrenergic increase in heart rate and contraction force. The Renin-Angiotensin-Aldosterone-System (RAAS) may be activated to induce vasoconstriction, fluid retention, and redistribution of blood flow. Although the neuro-endocrine response is compensatory, it may overload the cardiovascular system. This may result in myocardial damage, and may exacerbate CHF.

Diagnosing CHF may involve physical examination, electrocardiogram (ECG), blood tests, chest radiography, or echocardiography. Managing a CHF patient is challenging. CHF may require potent drugs. Moreover, treatment may be thwarted by the compensatory mechanisms, which may recompensate for the presence of the medical treatment. Therefore, treating CHF involves a delicate balance to properly manage the patient's hemodynamic status in a state of proper compensation to avoid further degeneration.

However, this delicate balance between compensation and effective CHF treatment is easily upset, even by seemingly benign factors, such as common medication (e.g., aspirin), physiological factors, excitement, or gradual progression of the disease. This may plunge the patient into a decompensation crisis, which requires immediate corrective action so as to prevent the deterioration of the patient's condition which, if left unchecked, can lead to death. In sum, accurately monitoring the symptoms of CHF, such as thoracic fluid accumulation, is very useful for avoiding such a decompensation crisis and properly managing the CHF patient in a state of relative well-being.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the term intravascular includes the term intracardiac.

In this document, the term cardiovascular includes an association with either the heart or a blood vessel.

In this document, the term "thorax" refers to a human subject's body other than the subject's head, arms, and legs.

Figure 1:
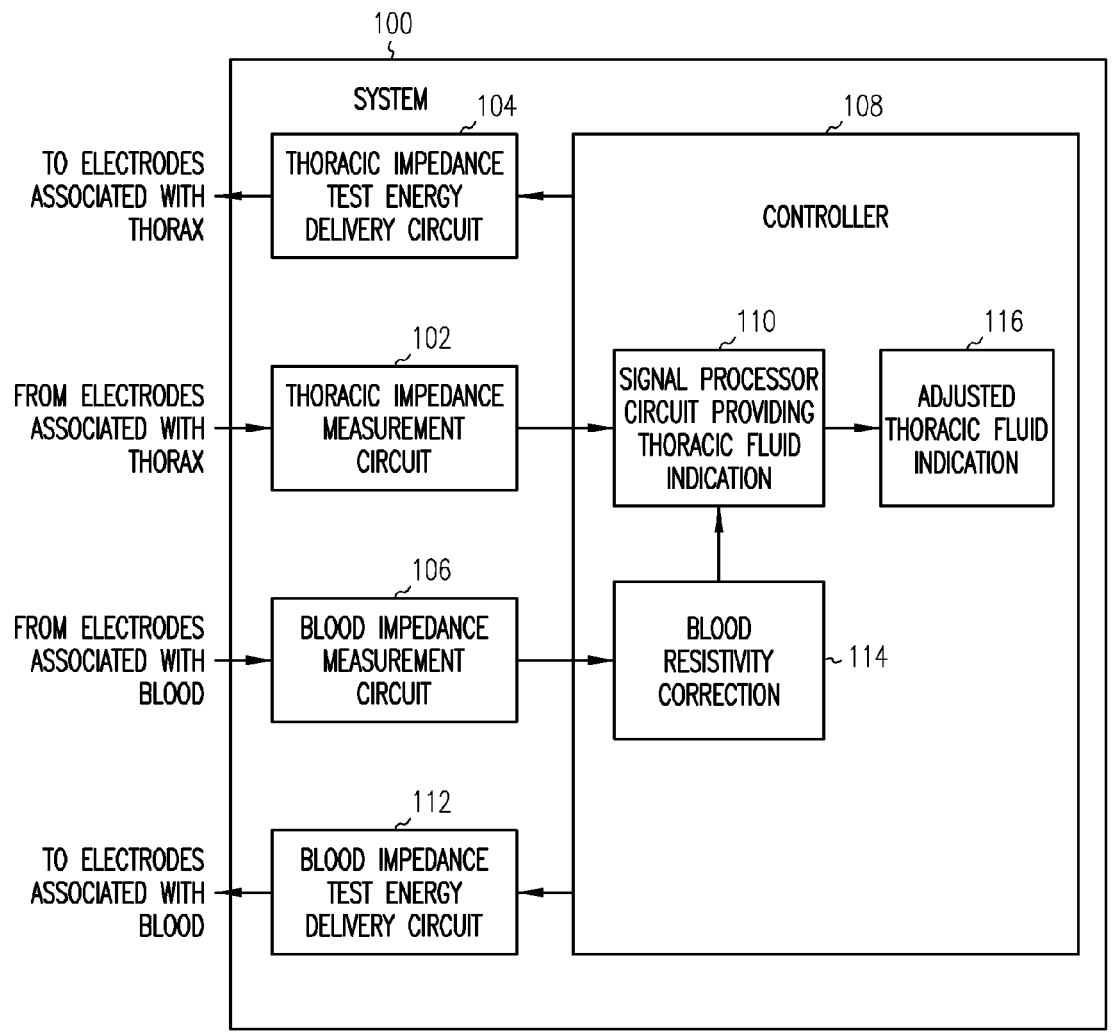
FIG. 1 is a block diagram illustrating generally one example of a system that provides a thoracic fluid amount indication that is adjusted to compensate for a change in blood resistivity, if any.

FIG. 1 is a block diagram illustrating generally one example of a system 100 that provides an indication of the amount of fluid in the thorax ("thoracic fluid indication") that is adjusted to compensate for a change in blood resistivity, if any. In this example, the system 100 includes a thoracic impedance measurement circuit 102. The thoracic impedance measurement circuit 102 receives at least one electrical signal from electrodes associated with a patient's thorax. This electrical signal is typically received in response to a test energy applied to the thorax, such as by a thoracic impedance test energy delivery circuit 104.

One illustrative example of some electrode configurations and circuits for performing thoracic impedance measurements is described in Hartley et al. U.S. Pat. No. 6,076,015 entitled RATE ADAPTIVE CARDIAC RHYTHM MANAGEMENT DEVICE USING TRANSTHORACIC IMPEDANCE, which is assigned to Cardiac Pacemakers, Inc., and which is incorporated herein by reference in its entirety, including its description of performing thoracic impedance measurements. The Hartley et al. U.S. Pat. No. 6,076,015 uses thoracic impedance to obtain a respiration signal. By contrast, the present patent application uses thoracic impedance to obtain a thoracic fluid status signal. Therefore, the signal of interest in the present patent application would be deemed noise in the Hartley et al. U.S. Pat. No. 6,076,015, and vice-versa. However, both thoracic fluid status and respiration are obtainable using the thoracic impedance detection techniques described in the Hartley et al. U.S. Pat. No. 6,076,015. The present thoracic fluid status signal of interest is obtained from a lower frequency (i.e., a "near-DC") portion of the thoracic impedance signal rather than the frequencies of the respiration signal described in the Hartley et al. U.S. Pat. No. 6,076,015. In this document, the "near-DC" component of the thoracic impedance signal refers to the frequencies below which respiration and cardiac contractions significantly influence the thoracic impedance signal. This near-DC component of the thoracic impedance signal, therefore, typically refers to signal frequencies below a cutoff frequency having a value of about 0.1 Hz, such as at signal frequencies between about $5 \times 10^{-7}$ Hz and 0.05 Hz, because the cardiac stroke and respiration components of the thoracic impedance signal lie at higher frequencies. Fluid accumulation in the thorax corresponds to a decrease in the near-DC thoracic impedance. Conversely, fluid depletion in the thorax corresponds to an increase in the near-DC thoracic impedance. As discussed above, fluid accumulation may result from, among other things, pulmonary edema or pleural effusion, both of which may result from CHF.

In the example of FIG. 1, the system 100 also includes a controller 108. The controller 108 is typically a microprocessor or any other circuit that is capable of sequencing through various control states such as, for example, by using a digital microprocessor having executable instructions stored in an associated instruction memory circuit, a microsequencer, or a state machine. In this example, the controller 108 includes a digital signal processor (DSP) circuit 110. The digital signal processor circuit 110 performs any digital filtering or other signal processing needed to extract from the thoracic impedance signal a near-DC desired thoracic fluid amount signal. The digital signal processor circuit 110, therefore, may implement one or more filter circuits, and such filter circuits may be implemented as a sequence of executable instructions, rather than by dedicated filtering hardware.

However, the present inventors have recognized that the near-DC thoracic impedance signal is typically also affected by confounding factors other than the amount of fluid present in the thorax. One such confounding factor is any change in blood resistivity. Blood resistivity changes as a function of hematocrit in the blood. The hematocrit (Ht) or packed cell volume (PCV) is the proportion of blood that is occupied by red blood cells. It is typically between 0.35 and 0.52, and is slightly higher on average in males than in females. For example, when a patient is dehydrated, there will be less fluid in the patient's blood. Therefore, the patient's hematocrit level will increase, that is, the patient's blood will include a higher percentage of other components, such as insulative red blood cells. This will increase the blood resistivity, which, in turn, will affect the thoracic impedance signal even though it is not necessarily associated with the extravascular fluid accumulation of pulmonary edema or pleural effusion. Other factors that are believed to possibly influence blood resistivity include the patient's electrolyte level, certain medications in the blood, proteins in the blood, or blood gas concentrations.

As an illustrative example, the above change in hematocrit percentage from 35% to 52% may correspond to a change in resistivity from about 140 Ω·cm to about 200 Ω·cm. Such changes in blood resistivity will influence the near-DC thoracic impedance measurement. This will confound an extravascular thoracic fluid amount determination using the near-DC thoracic impedance measurement, unless the extravascular thoracic fluid amount determination is corrected for such variations in blood resistivity, if any. Measurement of variations in blood resistivity is typically affected by the frequency of the excitation signal that are used. At higher excitation frequencies, blood cells typically become more resistive.

Accordingly, the system in FIG. 1 illustrates a blood resistivity measurement circuit 106. The blood impedance measurement circuit 106 receives a blood impedance measurement from electrodes that are associated with blood (and preferably blood in the thorax) such as in response to a delivery of test energy by a blood impedance test energy delivery circuit 112. In one example, the blood impedance measurement circuit 106 and the blood impedance test energy delivery circuit 112 are configured similar to the thoracic impedance measurement circuit 102 and the thoracic impedance test energy delivery circuit 104, respectively, as discussed above, except for being connected to different electrodes. Using the blood impedance measurement, the controller 108 executes a sequence of instructions to compute a blood resistivity correction 114. The blood resistivity correction 114 is applied to the thoracic fluid indication that is output by the digital signal processor circuit 110. This yields an adjusted thoracic fluid amount indication 116.

In FIG. 1, the thoracic impedance test energy delivery circuit 104 is illustrated separately from the blood impedance test energy delivery circuit 112 to assist the reader's conceptualization. In practice, these circuits, or portions thereof, may be combined. The combined circuit may be coupled to different electrodes for delivering the thoracic impedance test energy than for delivering the blood impedance test energy.

Similarly, in FIG. 1, the thoracic impedance measurement circuit 102 is illustrated separately from the blood impedance test energy delivery circuit 112 to assist the reader's conceptualization. In practice, these circuits, or portions thereof, may be combined. The combined circuit may be coupled to different electrodes for measuring the responsive voltages for the thoracic and blood impedance measurements, as discussed below.

Figure 2:
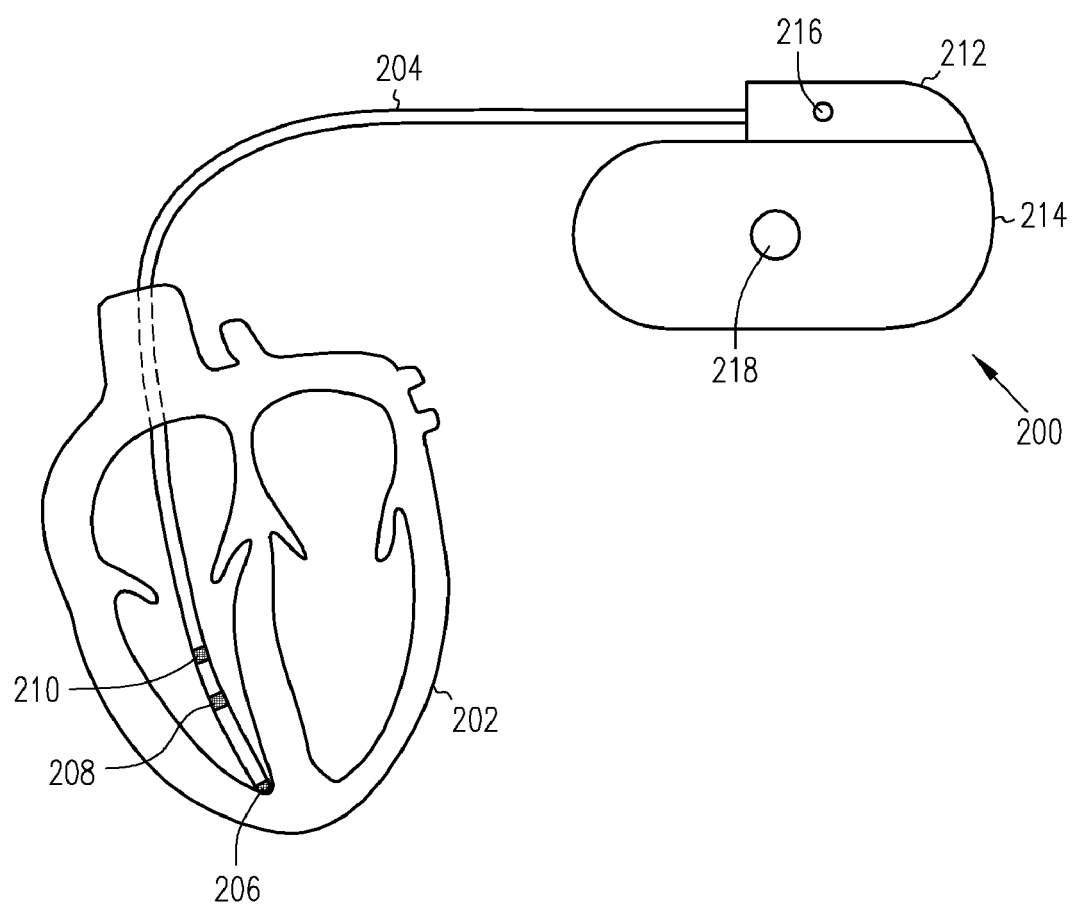
FIG. 2 is a schematic illustration of one example in which portions of the system are implemented in an implantable cardiac rhythm management (CRM) or other implantable medical device (IMD).

FIG. 2 is a schematic illustration of one example in which portions of the system 100 are implemented in an implantable cardiac rhythm management (CRM) or other implantable medical device (IMD) 200. In this example, the IMD 200 is coupled to a heart 202 using at least one leadwire, such as a multielectrode leadwire 204. In this example, the leadwire 204 includes a tip electrode 206, a distal ring electrode 208, and a proximal ring electrode 210, each of which is disposed in the right ventricle of the heart 202. In this example, each of the tip electrode 206, the distal ring electrode 208, and the proximal ring electrode 210 is independently electrically connected to a corresponding separate electrically conductive terminal within an insulating header 212. The header 212 is affixed to a housing 214 carrying electronic components of the IMD 200. In this example, the header 212 includes a header electrode 216, and the housing 214 includes a housing electrode 218.

In one example, thoracic impedance is sensed by delivering a test current between: (1) at least one of the ring electrodes 208 or 210; and (2) the housing electrode 218, and a resulting responsive voltage is measured across the tip electrode 206 and the header electrode 216. Because the IMD 200 is typically pectorally implanted at some distance away from the heart 202, this electrode configuration injects the test current over a substantial portion (but typically not the entire portion) of the patient's thorax, such that when the resulting voltage measurement is divided by the test current magnitude, it yields an indication of thoracic impedance. Using different electrodes for delivering the current and for measuring the responsive voltage reduces the component of the measured impedance signal that results from ohmic losses in the leadwires to the test current delivery electrodes. While such a "four-point" probe is useful, it is not required. In other examples, a "three-point probe" (having three electrodes, with one electrode used for both test current delivery and responsive voltage measurement), or a "two-point probe" (having two electrodes, each electrode used for both test current delivery and responsive voltage measurement) are used. Moreover, other electrode combinations could alternatively be used to implement a four-point probe. The above four-point probe description provides an illustrative example of one suitable four-point probe configuration.

In one example, blood impedance is sensed by delivering a test current between: (1) one of the distal ring electrode 208 or the proximal ring electrode 210; and (2) the housing electrode 218. A resulting responsive voltage is measured between: (1) the other of the distal ring electrode 208 or the proximal ring electrode 210; and (2) the tip electrode 206. In this example, although the test current is injected across a substantial portion of the patient's thorax, as discussed above, the responsive voltage signal of interest is measured across electrodes within the same chamber of the patient's heart (or, alternatively, within the same blood vessel). Therefore, when the responsive voltage measurement is divided by the test current magnitude, it yields an indication of the blood impedance in the heart chamber rather than the thoracic impedance. The measured blood impedance is used to compensate the measured thoracic impedance for changes in the blood impedance.

Figure 3:
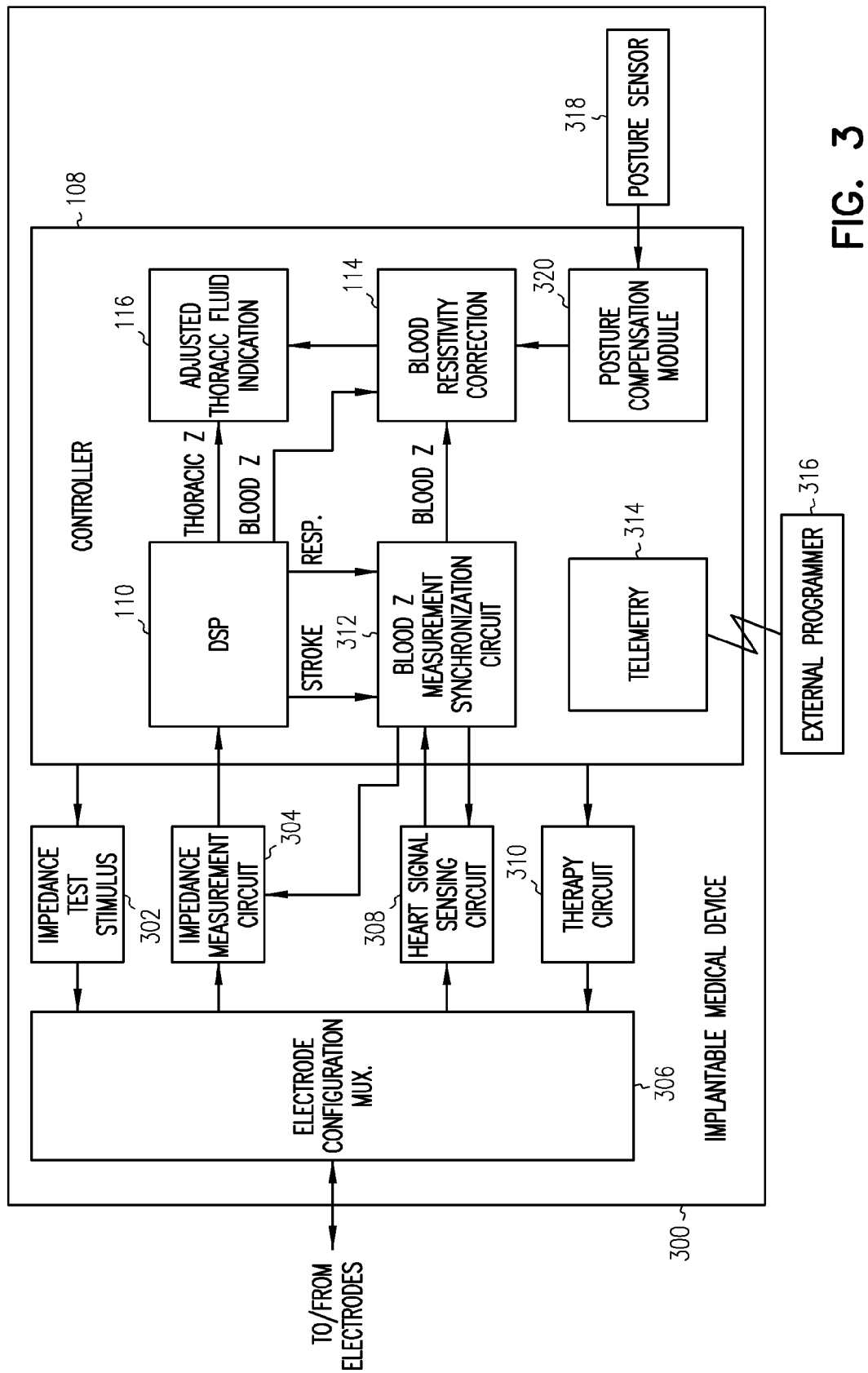
FIG. 3 is a block diagram illustrating generally another example in which portions of the system are implemented in an implantable CRM or other IMD.

FIG. 3 is a block diagram illustrating generally another example in which portions of the system 100 are implemented in an implantable CRM or other IMD 300. The example of FIG. 3 includes an impedance test stimulus circuit 302 that, together with an impedance measurement circuit 304, provides thoracic and blood impedance measurements. In response to one or more control signals from the controller 108, an electrode configuration multiplexer 306 couples these circuits to the appropriate electrodes for the particular thoracic or blood impedance measurement. In this example, the multiplexer 306 is also coupled to a heart signal sensing circuit 308, which includes sense amplifier or other circuits for detecting from particular electrodes intrinsic electrical heart signals that include electrical depolarizations corresponding to heart contractions. The multiplexer 306 is also coupled to a therapy circuit 310, such as a pulse delivery circuit for delivering pacing, cardioversion, or defibrillation energy to particular electrodes in response to one or more control signals received from the controller 108.

In the example of FIG. 3, the DSP circuit 110 processes the thoracic impedance measurements from the impedance measurement circuit 304. The DSP circuit 110 extracts a cardiac stroke signal or a respiration signal from the thoracic impedance signal, such as by using techniques described in the above-incorporated Hartley et al. U.S. Pat. No. 6,076,015. One or both of the extracted cardiac stroke or respiration signals is provided to a blood impedance measurement synchronization circuit 312. The synchronization circuit 312 includes one or more peak-detector, level-detector, or zero-cross detector circuits to synchronize the blood impedance measurement to the same sample point of a cardiac contraction cycle or a respiration cycle. This reduces the effect of variations in one or both of these cycles on the blood impedance measurement. Similarly, the measurements can be taken under the same conditions with respect to posture or circadian cycle to reduce those effects on the blood impedance measurement. Posture can be detected using an accelerometer or other posture sensor; circadian cycle can be ascertained from a time-of-day indication provided by a clock circuit within the controller 108. Alternatively, the cardiac cycle information is extracted from the heart signal sensing circuit 308, either by itself or in combination with information from the controller 108 about when pacing or other stimulus pulses that evoke a responsive heart contraction are issued. The controller 108 computes an adjusted thoracic fluid indication 116 from the measured thoracic impedance. The adjusted thoracic fluid indication 116 is compensated for blood resistivity variations using the blood resistivity correction 114 obtained using the measured blood impedance. In a further example, the implantable medical device 300 includes a telemetry circuit 314 that communicates one of the blood-resistivity-compensated thoracic impedance or the blood resistivity and thoracic impedance measurements to an external programmer 316 or the like for further processing, storage, or display.

Figure 4:
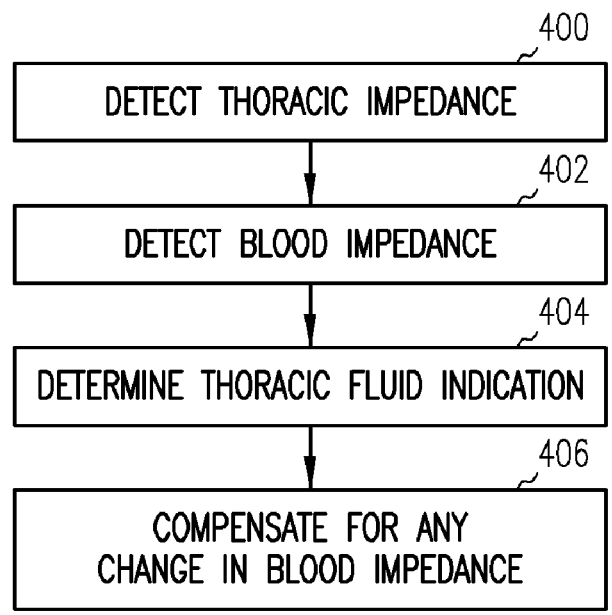
FIG. 4 is a flow chart illustrating generally one example of a method of providing a thoracic fluid amount indication that is compensated for any changes in blood resistivity.

FIG. 4 is a flow chart illustrating generally one example of a method of providing a thoracic fluid amount indication that is compensated for any changes in blood resistivity. At 400, a thoracic impedance is detected. This may be accomplished in a number of different ways. In one illustrative example, such as described in Hartley et al. U.S. Pat. No. 6,075,015, it includes injecting a four-phase carrier signal, such as between a housing electrode 218 and a ring electrode 208. In this example, the first and third phases are +320 microampere pulses that are 20 microseconds long. The second and fourth phases are −320 microampere pulses that are 20 microseconds long. The four phases are repeated at 50 millisecond intervals to provide a carrier test current signal from which a responsive voltage can be measured. However, as discussed elsewhere in this document, because blood resistivity varies with excitation frequency, a different excitation frequency may also be used.

The Hartley et al. U.S. Pat. No. 6,075,015 describes an exciter circuit for delivering such a test current stimulus (however, the present system can alternatively use other suitable circuits, including an arbitrary waveform generator that is capable of operating at different frequencies or of mixing different frequencies to generate an arbitrary waveform). It also describes a signal processing circuit for measuring a responsive voltage between a housing electrode 216 and a tip electrode 206. In one example, the signal processing circuit includes a preamplifier, demodulator, and bandpass filter for extracting the thoracic impedance data from the carrier signal, before conversion into digital form by an A/D converter. Further processing is performed digitally, and is performed differently in the present system 100 than in the Hartley et al. U.S. Pat. No. 6,075,015.

For example, the Hartley et al. U.S. Pat. No. 6,075,015 includes a bandpass filter that receives the output of the A/D converter. The purpose of the highpass portion of the bandpass filter is to attenuate the near-DC portion of the thoracic impedance signal, which is the signal of interest to the present system 100. Therefore, the present system 100 eliminates the highpass filter. The cutoff frequency of the remaining lowpass filter is selected to pass the near-DC portion of the thoracic impedance signal and attenuate higher frequency portions of the thoracic impedance signal, including the respiration and cardiac stroke components of the thoracic impedance signal. In one example, a programmable cutoff frequency lowpass filter is used. In another example, an adaptive cutoff frequency lowpass filter is used, such that the cutoff frequency is moved to a higher frequency for higher values of heart rate and respiration frequency, and the cutoff frequency is moved to a lower frequency for lower values of heart rate and respiration frequency.

At 402 of FIG. 4, blood impedance is detected and measured. There are a number of ways in which this can be done. In one example, the blood impedance measurement is performed in the same manner as the thoracic impedance measurement, except that measurement of the responsive voltage is across two electrodes that are both typically located in the same heart chamber or same blood vessel, such as between (1) one of the distal ring electrodes 208 or the proximal ring electrode 210; and (2) the other of the distal ring electrode 208 or the proximal ring electrode 210. Because the blood impedance is to be used to correct a thoracic fluid indication, it is typically detected and measured at or near the thorax. Alternatively, however, even an external blood impedance measurement could be used, if desired. In one example, the blood impedance is sampled under appropriate other conditions (e.g., at a like point in different cardiac cycles, at a like point in different respiration cycles, etc.).

At 404, a thoracic fluid amount indication is determined. There are a number of ways in which this can be done. In one example, the thoracic fluid amount indication is given by the value of the near-DC thoracic impedance signal, which may be averaged or otherwise filtered, if desired. In another example, a baseline value of this averaged or otherwise filtered near-DC thoracic impedance signal is obtained from the patient, and the thoracic fluid amount indication is given by the difference of the near-DC thoracic fluid impedance value (with the same or different averaging or filtering) from this baseline value.

At 406, the thoracic fluid amount indication obtained from the near-DC thoracic impedance is adjusted to compensate for changes in blood resistivity. In one example, the adjusted thoracic fluid amount indication is given by: $TFA_{adj} = TFA_{raw} \cdot (\rho_{Blood, current}) \div (\rho_{Blood, baseline})$. In this equation, $TFA_{adj}$ is the adjusted value of the thoracic fluid amount, $(\rho_{Blood, baseline})$ is the baseline value of the blood resistivity, and $(\rho_{Blood, current})$ is the current value of the blood resistivity. In the present case, since the same electrodes are used for both the baseline and current blood resistance measurements, the resistivity ratio $(\rho_{Blood, current}) \div (\rho_{Blood, baseline})$ is given by the corresponding ratio of the blood resistances, i.e., $(Z_{Blood, current}) \div (Z_{Blood, baseline})$.

In a further example, such as where the implantable medical device 300 optionally includes a posture sensor or detector 318, a separate baseline impedance or resistivity is provided for different postures, since posture affects thoracic impedance measurements. In one example, a separate baseline impedance or resistivity is stored for upright postures (e.g., sitting or standing) than for recumbent postures (e.g., supine, prone, left lateral decubitus, right lateral decubitus). In a further example, a separate baseline impedance or resistivity is stored for one or more of the different subtypes of upright or recumbent postures. In compensating the thoracic fluid amount indication, the posture compensation module 320 compensates a particular resistivity measurement by using a baseline resistivity that corresponds to the then-current posture indicated by the postures detector 318. One example of a suitable posture detector 318 is a commercially available two-axis accelerometer, such as Model No. ADXL202E, manufactured by Analog Devices, Inc. of Norwood, Mass., USA.

The compensated thoracic fluid amount indication can be stored in the implantable medical device 300 or transmitted to the external device 316. Moreover, in one example, the implantable medical device 300 or external device 316 is capable of storing a history of the values of the thoracic fluid amount indication to assist the physician in managing the CHF state of the patient. In one example, the external device 316 is capable of displaying a graph, histogram or other chart of such thoracic fluid amount values.

In a further example, the implantable medical device 300 or the external device 316 determines whether heart failure decompensation, pulmonary edema, or pleural effusion is present, such as by comparing an increase in the blood-resistivity-compensated thoracic fluid amount indication to a corresponding first threshold value to deem one or more of these conditions to be present.

In yet a further example, the implantable medical device 300 or the external device 316 predicts whether heart failure decompensation, pulmonary edema, or pleural effusion is likely to become present in the future, such as by comparing an increase in the blood-resistivity-compensated thoracic fluid amount indication to a corresponding second threshold value to deem one or more of these conditions to be likely in the future. The second threshold used for the condition prediction may be different from the first threshold used for the condition detection. In one example, the second threshold value reflects a smaller increase in the thoracic fluid amount indication than the first threshold value.

In yet a further example, the implantable medical device 300 adjusts a therapy to the patient using the thoracic fluid amount indication. In one example, an increase in the thoracic fluid amount indication triggers an increase in a rate at which pacing pulses are delivered to the heart. In another example, a change in the thoracic fluid amount indication results in altering another programmable parameter of cardiac pacing or cardiac resynchronization therapy, such as, for example, atrioventricular (AV) delay, particular cardiac stimulation sites, interventricular delay, or intraventricular delay. In a further example, a change in the thoracic fluid amount indication triggers the providing of a warning or other indication to the patient to adjust a medication level (for example, a diuretic).

Another application for the present systems, devices, and methods is in anemia detection. Anemia is a pathological condition that is often present in CHF patients. Diagnosing and treating anemia will improve a patient's cardiac function. Therefore, there is a need to detect anemia in CHF patients, for example, to communicate a diagnosis regarding the anemia status to a CHF patient's health care provider.

Figure 5:
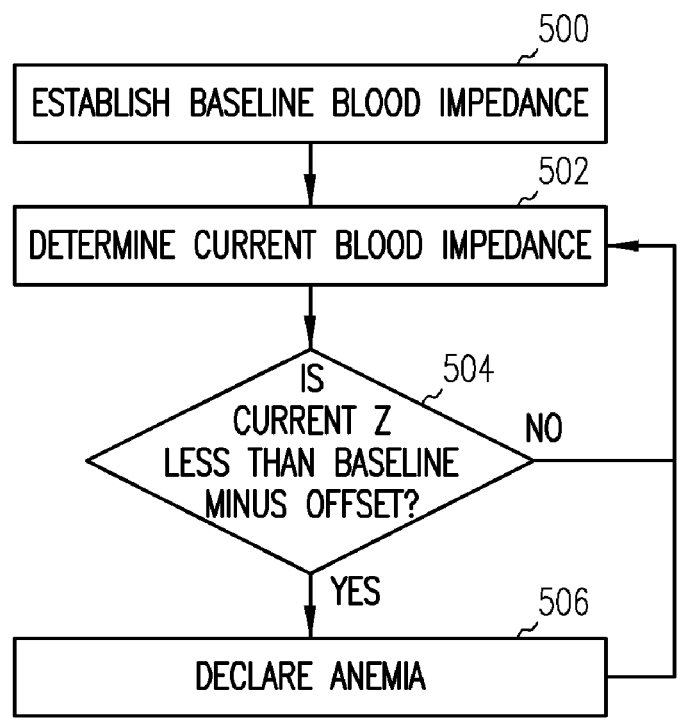
FIG. 5 is a flow chart illustrating generally one example of a method of detecting anemia using a blood impedance measurement performed by an implantable medical device.

FIG. 5 is a flow chart illustrating generally one example of an anemia detection method. At 500, a baseline blood impedance is established. In one example, this includes obtaining one or more near-DC blood impedance measurements (typically taken within the same blood vessel or heart chamber) such as described above with respect to 402 of FIG. 4. In one example, the baseline blood impedance is established by computing a central tendency (e.g., average, median, low-pass filtered, etc.) value of a series of such measured blood impedances over a desired time interval (for example, one month).

At 502, a current blood impedance is measured. This near-DC blood impedance measurement is typically performed in the same manner and location as described above for establishing the baseline. At 504, the current blood impedance is compared to the baseline blood impedance. As described above, a higher percentage of red blood cells tends to increase blood impedance. Therefore, when the current blood impedance falls far enough below the baseline blood impedance, then anemia may be indicated. Therefore, in one example, if the current blood impedance falls below the baseline blood impedance by at least an offset threshold value, then anemia is declared to be present at 506. In one example, the offset value is a fixed or programmable percentage of the baseline blood impedance (e.g., 5%, 10%, 20%, etc.). The offset value is typically set to prevent normal physiological variations in blood impedance from triggering an anemia detection. In another example, such as by choosing a different threshold value, the comparison predicts that anemia is likely to occur (e.g., if the blood impedance falls at least 10% below its baseline value, then future anemia is predicted; if the blood impedance then falls at least 20% below its baseline value, then present anemia is declared).

In one further example, if anemia is predicted or declared present, that information is telemetered or otherwise communicated to the patient's health care provider from the implantable medical device, such as by providing such information to an external device for storage or display. In one example, such communication takes place the next time that the implantable medical device is interrogated by a programmer or other external interface. In another example, such the implantable medical device itself initiates a telemetric or other communication of such information to an external device. In yet a further example, an anemia warning is provided to the patient, either directly by the implantable medical device (e.g., an audible warning), or via an external interface device.

In some examples, a method includes detecting a first blood resistivity at a first time using at least one implanted intravascular or intracardiac electrode in a patient. In an example, a second blood resistivity is detected at a second time using the at least one implanted intravascular or intracardiac electrode. In an example, the second blood resistivity is compared to the first blood resistivity. If the second blood resistivity is less than the first blood resistivity by at least a threshold value, then, in some examples, an indication or prediction of anemia is declared to be present in the patient. In an example, the first blood resistivity and the second blood resistivity are detected in the same blood vessel or heart chamber. In an example, the first blood resistivity and the second blood resistivity are detected under like conditions with respect to at least one of a cardiac cycle, a respiratory cycle, a posture, and a circadian cycle. In some examples, an indication of anemia predicted or anemia present is communicated to an external device.

In various examples, a system includes an implantable medical device. In an example, the implantable medical device includes first and second electrodes located within the same blood vessel or heart chamber. The implantable medical device, in an example, includes a blood resistivity measurement circuit configured to provide a blood resistivity signal obtained between the first and second electrodes at different first and second times. In an example, a controller is coupled to the blood resistivity measurement circuit and is configured to determine an indication or prediction of anemia by comparing a current blood resistivity to a stored baseline blood resistivity value. The blood resistivity measurement circuit, in some examples, includes a test current circuit to deliver a test current to first and second implantable electrodes. In further examples, the blood resistivity measurement circuit includes a voltage measurement circuit to measure a resulting voltage between third and fourth implantable electrodes. In an example, the system includes a heart signal sensing circuit configured to synchronize the first and second times to like portions of different cardiac cycles. In another example, the system includes a thoracic impedance measurement circuit configured to synchronize the first and second times to like portions of different respiration cycles. In still another example, the system includes a posture sensor and a posture compensation module configured to store different baseline blood resistivities corresponding to different postures obtained from the posture sensor.

As discussed above, measurement of variations in blood resistivity is typically affected by the frequency of the excitation signal that are used. At higher excitation frequencies, blood cells typically become more resistive. Therefore, to yield a more sensitive measurement of anemia, it may be desirable to use a higher excitation frequency than would be used for detecting thoracic impedance, and for correcting the resulting thoracic impedance measurements for changes in blood resistivity. Alternatively, such as for measuring thoracic fluid status, if a change in blood resistivity exceeds a certain threshold value then, in one example, the system automatically switches to a lower excitation frequency that is affected less by changes in blood resistivity.

Although much of the above discussion has emphasized correcting near-DC thoracic impedance measurements to account for changes in blood resistivity, hematocrit-related blood resistivity changes may also affect higher frequency components of the thoracic impedance signal (e.g., respiration components, cardiac stroke components, etc.), somewhat analogous to the way in which patient posture can affect such higher frequency components of the thoracic impedance signal. Aspects of the present blood resistivity measurement and correction techniques may also be used for correcting such higher-frequency components of the thoracic impedance signal. However, the effects of blood resistivity changes at higher frequency may be nonlinear, making correction with a single multiplicative correction factor difficult or impossible. Therefore, a nonlinear correction function may be used, if needed. Such a nonlinear correction function may be empirically determined. In one example, the nonlinear correction function may be implemented as a lookup table. Moreover, the higher-frequency components of the thoracic impedance signal may be used to infer thoracic fluid status even much of the above discussion focused on particular examples that extract a thoracic fluid status signal from the near-DC component of the thoracic impedance signal.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in this document and in the following claims, the terms "first," "second," and "third," etc. are used merely as labels, and are not intended to impose numerical requirements on their objects.

What is claimed is:

1. A method comprising:
   obtaining a first blood resistivity quantity during a first time using at least one implanted intravascular or intracardiac electrode in a subject;
   obtaining a second blood resistivity quantity during a second time using the at least one implanted intravascular or intracardiac electrode;
   comparing, using a controller, the second blood resistivity quantity to the first blood resistivity quantity; and
   declaring an indication or prediction of anemia to be present in the patient when the second blood resistivity quantity is less than the first blood resistivity quantity by at least a first amount.

2. The method of claim 1, wherein obtaining the first blood resistivity quantity and obtaining the second blood resistivity quantity are performed in the same blood vessel or heart chamber.

3. The method of claim 1, wherein obtaining the first blood resistivity quantity and obtaining the second blood resistivity quantity are performed under a like condition with respect to at least one of a cardiac cycle, a respiratory cycle, a posture, and a circadian cycle.

4. The method of claim 1, comprising communicating an indication of anemia predicted or anemia present to an external device.

5. The method of claim 1, wherein declaring an indication or prediction of anemia includes:
   declaring an indication of anemia to be present in the patient when the second blood resistivity quantity is less than the first blood resistivity quantity by at least a second amount; and
   declaring a prediction of anemia to be present in the patient when the second blood resistivity quantity is less than the first blood resistivity quantity by at least the first amount and by less than the second amount.

6. The method of claim 1, comprising communicating information regarding the indication or prediction of anemia.

7. The method of claim 1, comprising displaying information regarding the indication or prediction of anemia.

8. The method of claim 7, wherein displaying the information includes displaying the information using an external device.

9. The method of claim 1, comprising providing an anemia warning with the indication or prediction of anemia.

10. The method of claim 1, wherein at least one of:
    obtaining the first blood resistivity quantity includes detecting a first blood resistivity measurement during the first time; or
    obtaining the second blood resistivity quantity includes detecting a second blood resistivity measurement during the second time.

11. The method of claim 1, wherein at least one of:
    obtaining the first blood resistivity quantity includes combining two or more first blood resistivity measurements acquired during the first time; or
    obtaining the second blood resistivity quantity includes combining two or more second blood resistivity measurements acquired during the second time.

12. The method of claim 1, wherein at least one of:
    obtaining the first blood resistivity quantity includes averaging two or more first blood resistivity measurements acquired during the first time; or
    obtaining the second blood resistivity quantity includes averaging two or more second blood resistivity measurements acquired during the second time.

13. An implantable medical device comprising:
    a blood resistivity measurement circuit configured to provide a blood resistivity signal using first and second electrodes;
    a controller coupled to the blood resistivity measurement circuit, the controller configured to determine an indication or prediction of anemia by comparing a second blood resistivity quantity to an earlier first blood resistivity quantity; and
    a communication circuit coupled to the controller, the communication circuit configured to communicate the indication or prediction of anemia to an external interface device.

14. The implantable medical device of claim 13, wherein the first and second electrodes are located within the same blood vessel or heart chamber.

15. The implantable medical device of claim 13, wherein the first and second electrodes are included on a leadwire.

16. The implantable medical device of claim 15, wherein the first electrode includes a ring electrode and the second electrode includes a tip electrode.

17. The implantable medical device of claim 15, comprising:
    a third electrode included on a housing of the implantable medical device; and
    a fourth electrode included on the leadwire;
    a test current circuit configured to deliver a test current between the third and fourth electrodes; and
    a voltage measurement circuit configured to measure a resulting voltage between the first and second electrodes.

18. The implantable medical device of claim 17, wherein the fourth electrode includes a ring electrode.

19. The implantable medical device of claim 13, comprising a heart signal sensing circuit configured to synchronize the first and second times to like portions of different cardiac cycles.

20. The implantable medical device of claim 13, comprising a posture sensor and a posture compensation module configured to store different first blood resistivity quantities corresponding to different postures obtained from the posture sensor.

21. The implantable medical device of claim 13, comprising a thoracic impedance measurement circuit configured to synchronize the first and second times to like portions of different respiration cycles.

22. The implantable medical device of claim 13, wherein at least one of:
the first blood resistivity quantity includes a first blood resistivity measurement detected during the first time; or
the second blood resistivity quantity includes a second blood resistivity measurement detected during the second time.

23. The implantable medical device of claim 13, wherein at least one of:
the first blood resistivity quantity includes a combination of two or more first blood resistivity measurements acquired during the first time; or
the second blood resistivity quantity includes a combination of two or more second blood resistivity measurements acquired during the second time.

24. The implantable medical device of claim 13, wherein at least one of:
the first blood resistivity quantity includes an average of two or more first blood resistivity measurements acquired during the first time; or
the second blood resistivity quantity includes an average of two or more second blood resistivity measurements acquired during the second time.

25. A system comprising:
means for obtaining a first blood resistivity quantity during a first time using at least one implanted intravascular or intracardiac electrode in a subject;
means for obtaining a second blood resistivity quantity during a second time using the at least one implanted intravascular or intracardiac electrode;
means for comparing the second blood resistivity quantity to the first blood resistivity quantity; and
means for declaring an indication or prediction of anemia to be present in the patient when the second blood resistivity quantity is less than the first blood resistivity quantity by at least a first amount.

26. The system of claim 25, wherein the means for declaring the indication or prediction of anemia includes:
means for declaring an indication of anemia to be present in the patient when the second blood resistivity quantity is less than the first blood resistivity quantity by at least a second amount; and
means for declaring a prediction of anemia to be present in the patient when the second blood resistivity quantity is less than the first blood resistivity quantity by at least the first amount and by less than the second amount.

27. The system of claim 25, comprising means for communicating information regarding the indication or prediction of anemia.

28. The system of claim 25, wherein at least one of:
the means for obtaining the first blood resistivity quantity includes means for detecting a first blood resistivity measurement during the first time; or
the means for obtaining the second blood resistivity quantity includes means for detecting a second blood resistivity measurement during the second time.

29. The system of claim 25, wherein at least one of:
the means for obtaining the first blood resistivity quantity includes means for combining two or more first blood resistivity measurements acquired during the first time; or
the means for obtaining the second blood resistivity quantity includes means for combining two or more second blood resistivity measurements acquired during the second time.

30. The system of claim 25, wherein at least one of:
the means for obtaining the first blood resistivity quantity includes means for averaging two or more first blood resistivity measurements acquired during the first time; or
the means for obtaining the second blood resistivity quantity includes means for averaging two or more second blood resistivity measurements acquired during the second time.

* * * * *